(12) United States Patent
Albertorio

(10) Patent No.: US 8,048,157 B2
(45) Date of Patent: Nov. 1, 2011

(54) TUNNEL MEASURING DEVICE FOR LIGAMENT RECONSTRUCTION

(75) Inventor: Ricardo Albertorio, Naples, FL (US)

(73) Assignee: Arthrex, Inc., Naples, FL (US)

( * ) Notice: Subject to any disclaimer, the term of this patent is extended or adjusted under 35 U.S.C. 154(b) by 488 days.

(21) Appl. No.: 12/252,214

(22) Filed: Oct. 15, 2008

(65) Prior Publication Data
US 2009/0099556 A1 Apr. 16, 2009

Related U.S. Application Data

(63) Continuation-in-part of application No. 12/030,773, filed on Feb. 13, 2008.

(60) Provisional application No. 60/980,107, filed on Oct. 15, 2007, provisional application No. 60/900,988, filed on Feb. 13, 2007.

(51) Int. Cl.
A61F 2/08 (2006.01)
A61F 2/00 (2006.01)
A61B 17/58 (2006.01)
A61B 17/60 (2006.01)

(52) U.S. Cl. ..................... 623/13.11; 606/102

(58) Field of Classification Search .................. 606/102; 623/13.11
See application file for complete search history.

(56) References Cited

U.S. PATENT DOCUMENTS

| 5,306,301 A * | 4/1994 | Graf et al. ..................... 606/232 |
| 5,643,273 A * | 7/1997 | Clark .............................. 606/96 |
| 6,716,234 B2 | 4/2004 | Grafton et al. |
| 7,401,413 B1 * | 7/2008 | Nelson ............................ 33/512 |
| 2004/0199166 A1 * | 10/2004 | Schmieding et al. ........... 606/79 |
| 2007/0016208 A1 | 1/2007 | Thornes |
| 2008/0208204 A1 | 8/2008 | Schmieding et al. |

* cited by examiner

Primary Examiner — David Isabella
Assistant Examiner — Leslie Coburn
(74) Attorney, Agent, or Firm — Dickstein Shapiro LLP

(57) ABSTRACT

Measuring devices and methods of determining the appropriate graft length for reconstructive surgery, for example for an all-inside ACL reconstruction ligament repair. The measuring device accurately determines the graft length based on the total length between the femoral and tibial tunnels (sockets) plus the intraarticular space between them. The measuring device may comprise two small, cannulated beads (preferably polished metal) and three strands (for example, three suture strands). The beads may have a diameter of about 5 mm and the three sutures may preferably have distinct and different colors.

10 Claims, 5 Drawing Sheets

TUNNEL MEASURING DEVICE FOR LIGAMENT RECONSTRUCTION

CROSS-REFERENCE TO RELATED APPLICATIONS

This application claims the benefit of U.S. Provisional Application No. 60/980,107, filed Oct. 15, 2007, the entire disclosure of which is incorporated by reference herein. This application is also a continuation-in-part application of U.S. application Ser. No. 12/030,773, filed Feb. 13, 2008 (U.S. Publication No. 2008/0208204; which in turn claims the benefit of U.S. Provisional Application No. 60/900,988, filed Feb. 13, 2007, the entire disclosures of which are also incorporated by reference herein.

FIELD OF THE INVENTION

The present invention relates to the field of surgery and, more particularly, to methods of reconstructive ligament surgeries.

BACKGROUND OF THE INVENTION

Reconstructive knee surgeries, particularly anterior cruciate ligament (ACL) reconstruction, are well-known in the art. In general, these methods of tenodesis involve drilling a tunnel through the tibia, drilling a closed tunnel (socket) into the femur, inserting a substitute ACL graft into the tunnels, and securing the graft to the walls of the tibial and femoral tunnels using interference screws or the like.

Fixation of the graft (for example, a semitendonosus allograft) within the two knee sockets (i.e., the femoral and tibial tunnels or sockets) requires determination of the proper graft length (soft tissue graft or BTB graft) which in turn is calculated based on the entire length of the sockets plus the intraarticular space between them. Proper determination of the graft length ensures accurate placement of the graft within the femoral and tibial tunnels (sockets).

BRIEF SUMMARY OF THE INVENTION

The present invention provides methods and measuring devices for determining the appropriate graft length for reconstructive surgeries, for example for reconstructive knee surgeries during ligament repair. The measuring device of the present invention comprises two measuring elements and three strands of flexible material attached to the elements. The measuring device of the present invention accurately determines the graft length based on the total length between two sockets formed in two articulating bones of a joint plus the intraarticular space between them.

These and other features and advantages of the invention will be more apparent from the following detailed description that is provided in connection with the accompanying drawings and illustrated exemplary embodiments of the invention.

DETAILED DESCRIPTION OF THE INVENTION

Figure 1:
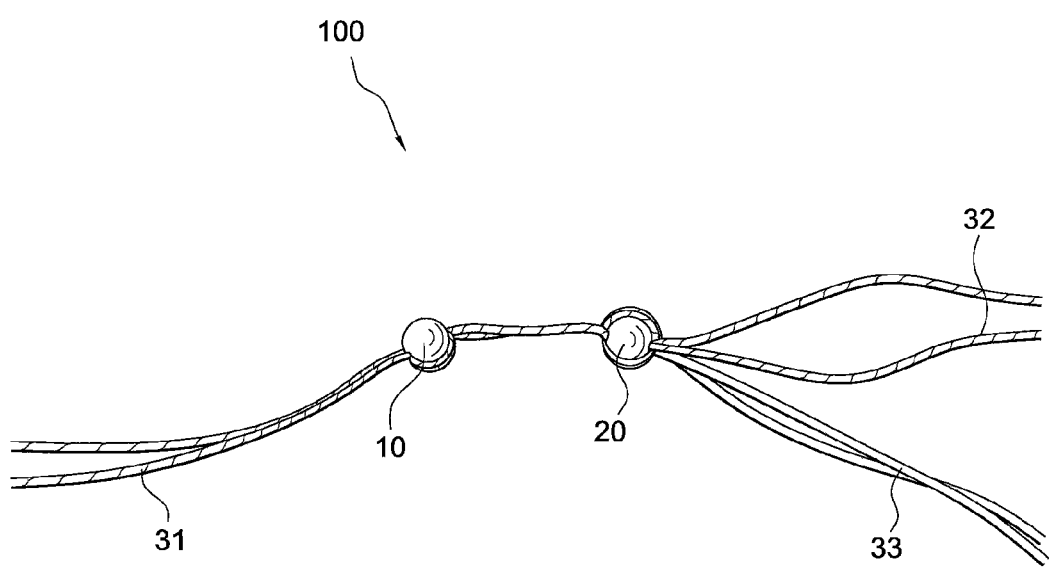
FIG. 1 illustrates an exemplary embodiment of a measuring device of the present invention.

The present invention provides methods and measuring devices for determining the appropriate graft length for reconstructive surgeries, for example for reconstructive knee surgeries (such as an all-inside ACL reconstruction ligament repair). The measuring device of the present invention comprises two measuring elements and three strands of flexible material (for example, suture) attached to the elements. The measuring device of the present invention accurately determines the graft length based on the total length between two sockets formed in two articulating bones (for example, femoral and tibial sockets or tunnel) of a joint plus the intraarticular space between them.

In an exemplary embodiment, the measuring device of the present invention comprises at least two measuring elements wherein at least one of the measuring elements is a cannulated element, to allow the cannulated element to move along a strand of flexible material (for example, suture) attaching the cannulated element to one of the other measuring elements. In yet another embodiment, two of the measuring elements are cannulated elements, in an exemplary embodiment only, one of the measuring elements is a fixed element (i.e., a static element that does not move along the length of the flexible strand) whereas the other element is a movable element (i.e., it moves from a first position to a second position along the flexible strand, and relative to the fixed element).

The measuring elements of the present invention may have any form, shape and geometry that allows the measuring elements to affix to a strand of flexible material (in a fixed way, for the fixed element, or in moveable way, for the moveable element). For example, the elements may be attached to the flexible strand by affixing or clipping the elements to the strand. In yet additional embodiments, the elements may be provided with a cannulation to allow a strand of flexible material to be threaded through the cannulation. In other embodiments, one measuring element may be a knot (formed in the same flexible strand, or formed with a different strand), whereas the other measuring element is a cannulated element configured to slide or move along the flexible strand and relative to the knot.

The moveable element may be a structure with any shape or configuration (for example, cylindrical, spherical or oval, among many others) as long as it is configured to be attached to the strand and move along at least a portion of the strand. For example, the moveable element may be a small, cannulated bead whereas the fixed element may be also a small, cannulated bead. In an exemplary embodiment only, the measuring device of the present invention comprises two small, cannulated beads (preferably of polished metal) and three strands of flexible material (for example, three suture strands) attached to the beads. The beads may have a diameter of about 5 mm and the three sutures may preferably have distinct colors (e.g. tigertail, blue or green, among others). The suture is configured such that one bead is fixed or static (for example, the proximal bead) and the other bead (for example, the distal bead) may move along the central section of the suture when tension is applied to the opposing suture tails. A third suture is attached to the movable bead and serves to remove the construct from the joint space once the tunnel measurement is complete. When tension is applied to the proximal suture and the removal suture, the moveable bead is locked in position.

The present invention also provides a method of measuring the total length between two sockets or tunnels formed in two articulating bones (for example, the femoral and tibial tunnels or sockets) plus the intraarticular space between them, by employing a measuring device comprising two measuring elements (for example, two spherical elements) and three strands of flexible material (for example, three suture strands).

The present invention also provides a method of ACL reconstruction comprising, for example, the steps of: (i) drilling femoral and tibial tunnels or sockets (using a retrodrill technique, for example); (ii) employing a measuring device (comprising two measuring elements and three strands of flexible material) to determine the entire length of the sockets plus the intraarticular space to subsequently determine the length of the graft (soft tissue graft or BTB graft) based on the entire length of the sockets plus the intraarticular space between them; and (iii) securing the graft within the femoral and tibial tunnels (sockets).

According to another embodiment, a method of ACL reconstruction of the present invention comprises, for example, the steps of: (i) drilling at least a femoral and tibial tunnel or socket using a retrodrill technique, for example; (ii) employing a measuring device (comprising two measuring elements and three flexible strands) to determine the entire length of the sockets plus the intraarticular space to subsequently determine the length of the graft (soft tissue graft or BTB graft) based on the entire length of the sockets plus the intraarticular space between them: (iii) securing the graft (soft tissue graft or BTB graft) to a continuous loop/button construct comprising a button with an oblong configuration and provided with an inside eyelet that allows the passage of the continuous loop, preferably a suture loop; (v) passing the graft with the button through the femoral tunnel; (vi) securing the button to the femoral cortex once the button exits the femoral socket; and (vii) securing the graft in the tibial tunnel or socket.

Referring now to the drawings, where like elements are designated by like reference numerals, FIGS. 1-9 illustrate exemplary embodiments of measuring device 100 of the present invention comprising two measuring elements 30, 20 and three flexible strands 31, 32, 33. As shown in FIG. 1, the two measuring elements 10, 20 are two small, cannulated beads 10, 20 (preferably polished metal) and the three strands 31, 32, 33 correspond the proximal, removal and distal strands, respectively. At least one of the strands (and preferably all three strands) is a suture strand. The beads 10, 20 may have a diameter of about 5 mm and the three strands 31, 32, 33 may preferably have distinct colors (e.g. tigertail, blue, or green, among others).

The suture strands are configured such that one bead (for example, proximal bead 10) is fixed or static and the other bead (for example, distal bead 20) may move along the central section of the suture when tension is applied to the opposing suture tails. A third suture 32 is attached to the movable bead and serves to remove the construct 100 from the joint space once the tunnel measurement is complete. When tension is applied to the proximal suture 31 and the removal suture 32, the moveable bead 20 is locked in position.

Figure 2:
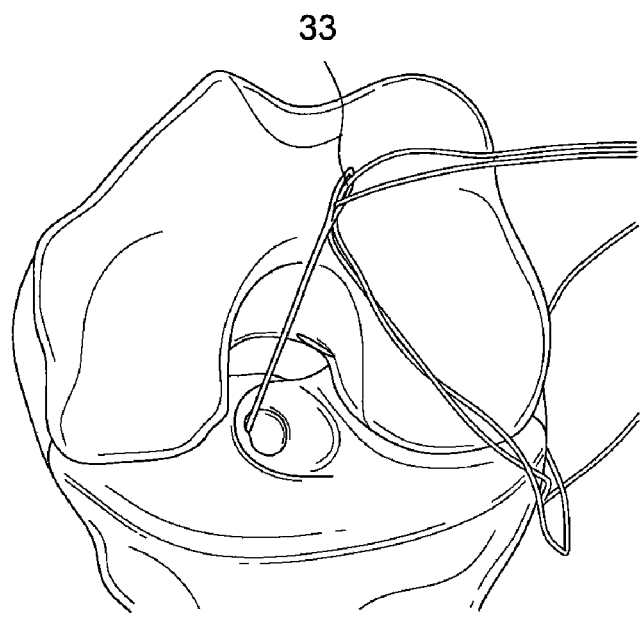
FIGS. 2-9 illustrate various steps of a method of determining the length of a graft (calculated based on the entire length of a first and second socket plus the intraarticular space between them) by employing the measuring device of FIG. 1.

An exemplary method of measuring the total length between the femoral and tibial tunnels (sockets) plus the intraarticular space between them, by employing the tunnel measuring device 100 of the present invention, is detailed below with reference to FIGS. 2-9:

FIG. 2: Distal suture 33 is passed into knee through an arthroscopic portal, and subsequently into the tibial socket, exiting percutaneously through the 3 mm tunnel created during retrodrilling.

Figure 3:
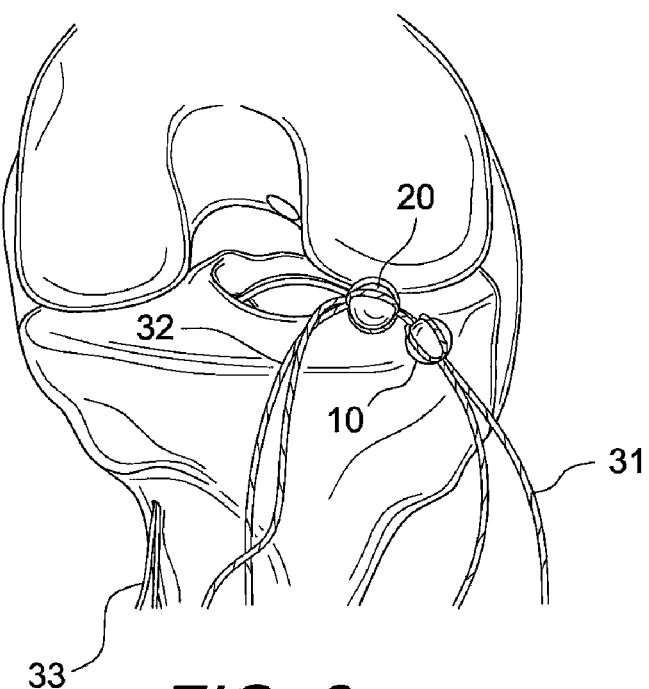

FIG. 3: Construct 100 is pulled into the knee through the arthroscopic portal; the removal suture strands 32 are left exiting the portal anteriorly.

Figure 4:
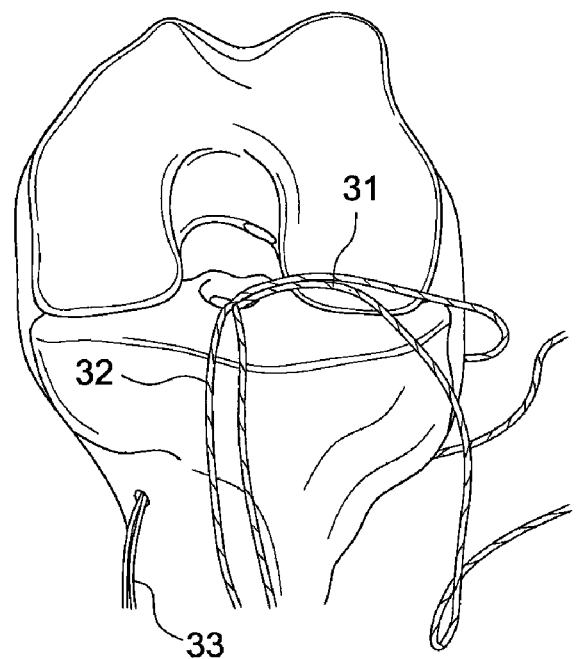

FIG. 4: The beads 10, 20 are retracted into the tibial socket by pulling on the distal suture strands 33 until the distal bead 20 bottoms out.

Figure 5:
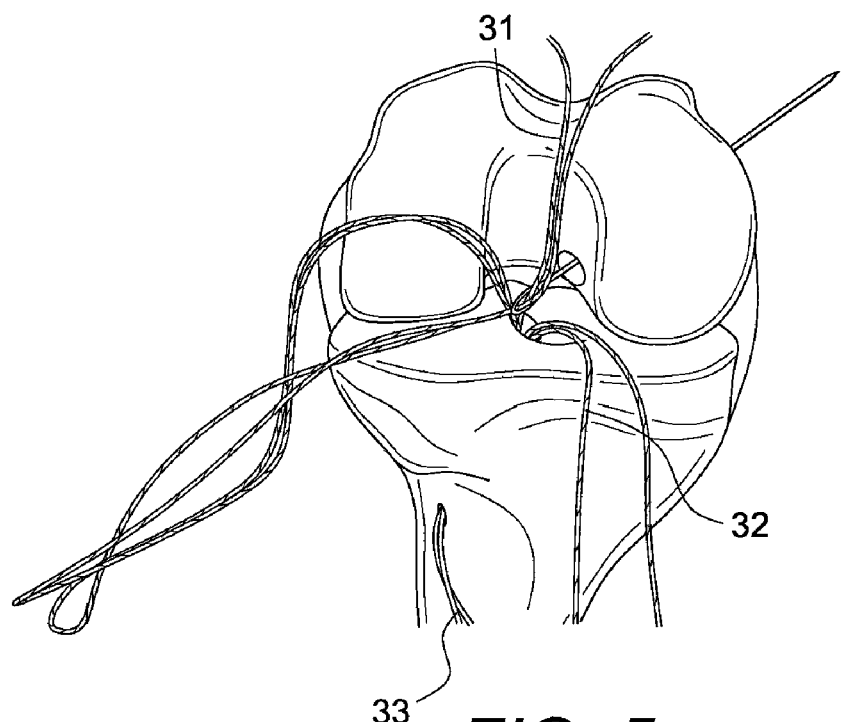

FIG. 5: The proximal suture 31 is passed into the femoral socket in the same manner as in FIG. 2 above.

Figure 6:
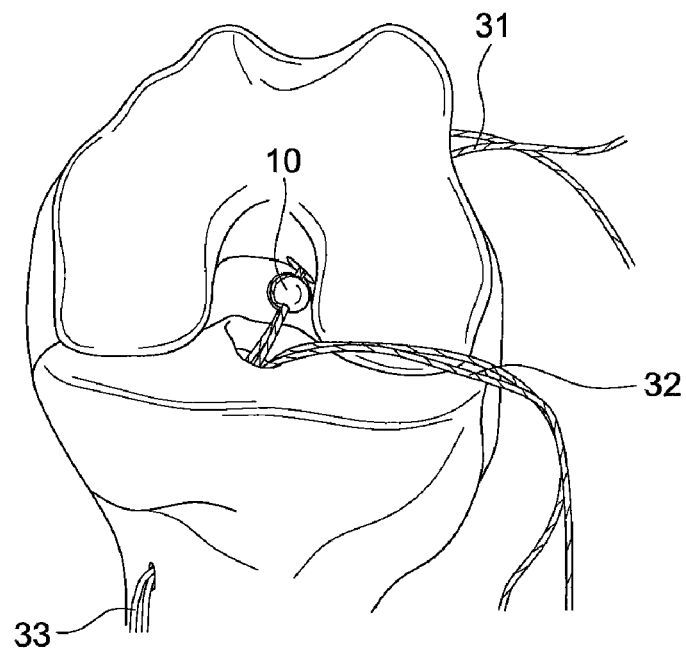

FIG. 6: The knee is positioned in about 90° of flexion. While maintaining tension on distal suture 33, the proximal suture 31 is pulled taut, causing the proximal bead 10 to move into the femoral tunnel.

Figure 7:
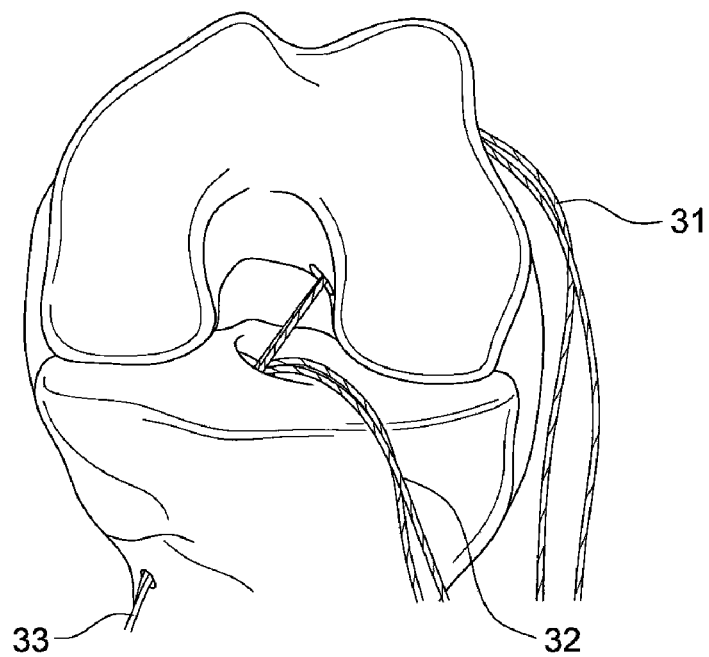

FIG. 7: Proximal bead 10 is bottomed out in the femoral tunnel.

Figure 8:
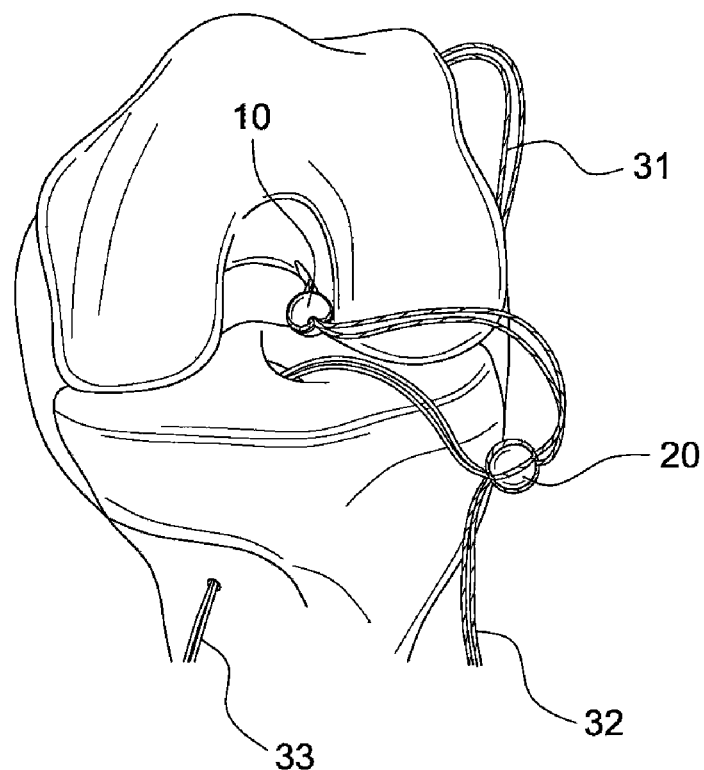

FIG. 8: With the tension released on the distal suture 33 yet maintained on the proximal suture 31, the removal suture 32 is pulled to extract the distal bead 20 from the tibial tunnel and remove the assembly 100 from the joint.

Figure 9:
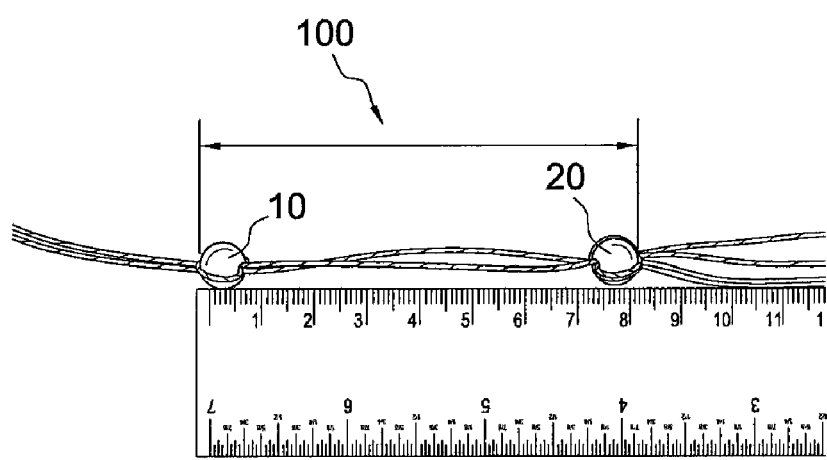

FIG. 9: The outside distance between beads 10, 20 is measured to estimate required graft length.

The present invention also provides a method of ACL reconstruction comprising, for example, the steps of: (i) drilling femoral and tibial tunnels or sockets (using a retrodrill technique, for example); (ii) employing tunnel measuring device 100 comprising two small beads 10, 20 and three suture strands 31, 32, 33, to determine the entire length of the sockets plus the intraarticular space to subsequently determine the length of the graft (soft tissue graft or BTB graft) based on the entire length of the sockets plus the intraarticular space between them; and (iii) securing the graft within the femoral and tibial tunnels (sockets).

According to another embodiment, a method of ACL reconstruction of the present invention comprises, for example, the steps of: (i) drilling at least a femoral and tibial tunnel or socket using a retrodrill technique, for example; (ii) employing measuring device 100 comprising two small beads 10, 20 and three suture strands 31, 32, 33, to determine the entire length of the sockets plus the intraarticular space to subsequently determine the length of the graft (soft tissue graft or BTB graft) based on the entire length of the sockets plus the intraarticular space between them; (iii) securing the graft (soft tissue graft or BTB graft) to a continuous loop/button construct comprising a button with an oblong configuration and provided with an inside eyelet that allows the passage of the continuous loop, preferably a suture loop; (v) passing the graft with the button through the femoral tunnel; (vi) securing the button to the femoral cortex once the button exits the femoral socket; and (vii) securing the graft in the tibial tunnel or socket.

Details of the formation of the femoral and tibial tunnels or sockets employing an all-inside technique are set forth in U.S. application Ser. No. 12/165,107, filed on Jun. 30, 2008, entitled "Double Socket ACL Reconstruction," the entire disclosure of which is incorporated by reference herein.

In an exemplary embodiment, at least one of the suture strands 31, 32, 33 (and preferably each of the suture strands) is a single high strength suture such as FiberWire® suture, sold by Arthrex, Inc. of Naples, Fla., and described in U.S. Pat. No. 6,716,234, the disclosure of which is incorporated by reference herein. In another exemplary embodiment, suture strands 31, 32, 33 may be formed of a plurality of suture strands, at least one of the plurality of suture strands being a FiberWire® suture.

The formation of the femoral and tibial sockets or tunnels may be conducted by either a conventional method or a retrograde method. The sockets may be formed using a retrodrill cutter which is inserted in a retrograde manner through tibia and/or femur, and as detailed in U.S. Patent Application Publication No. 2004/0199166, entitled "ACL Reconstruction Technique Using Retrodrill."

Once the tibial and the femoral socket are formed, the length of the graft (soft tissue grafts and/or BTB grafts) that will be secured within the tibial and femoral sockets is determined based on the entire length of the sockets plus the intraarticular space between them. The selected graft is then secured within the femoral tunnel (socket) by using various fixation devices such as a continuous loop/button construct (retrobutton). The other end of the graft may be secured within the tibial sockets by employing an interference fixation device such as interference screw.

Although the present invention has been described in connection with preferred embodiments, many modifications and variations will become apparent to those skilled in the art. While preferred embodiments of the invention have been described and illustrated above, it should be understood that these are exemplary of the invention and are not to be considered as limiting. Accordingly, it is not intended that the present invention be limited to the illustrated embodiments, but only by the appended claims.

What is claimed as new and desired to be protected by Letters Patent of the United States is:

1. A method of conducting surgery, comprising the steps of:
   forming a first bone socket in a first bone;
   forming a second bone socket in a second bone, the first bone articulating in a predetermined manner with the second bone;
   providing a measuring device in the vicinity of the first and second bone sockets, the measuring device comprising two cannulated spheres operatively connected by three strands of suture;
   employing the measuring device to determine a total length which is about equal to the length of the first and second sockets plus the intraarticular space between the first and second sockets; and
   based on the total length, determining a length of a graft to be positioned within the first and second bone sockets wherein employing the measuring device includes positioning one of the cannulated spheres at one end of the first socket;
   positioning the other of the cannulated spheres at one end of the second socket;
   then pulling taut at least one of the strands connecting the two cannulated spheres and measuring the total length as the distance between the two cannulated spheres.

2. The method of claim 1, wherein one of the two cannulated spheres is fixed relative to one of the strands, and the other of the two cannulated spheres is movable relative to the one of the strands.

3. The method of claim 1, further comprising the steps of:
   securing one end of the graft within the first bone socket by employing a first fixation device selected from the group consisting of a transversal implant, an interference screw and a suture loop/button construct; and
   securing the other end of the graft within the second bone socket by employing a second fixation device selected from the group consisting of an interference screw and a suture loop/button construct.

4. The method of claim 1, wherein at least one of the first and second bone sockets is formed by drilling in a retrograde manner using a rotary drill cutter.

5. The method of claim 1, wherein the graft is biological or non-biological tissue.

6. The method of claim 1, wherein the graft is at least one of ligament, tendon, bone or cartilage.

7. The method of claim 1, wherein the graft is a soft tissue graft or BTB graft.

8. The method of claim 1, wherein the first bone is a femur and the second bone is a tibia.

9. A method of ACL reconstruction, comprising the steps of:
   forming a first bone socket in a first bone;
   forming a second bone socket in a second bone, the first bone articulating in a predetermined manner with the second bone, wherein at least one of the first and second bone sockets is formed by drilling in a retrograde manner using a rotary drill cutter;
   providing a measuring device in the vicinity of the first and second bone sockets, the measuring device comprising two cannulated spheres operatively connected by three flexible strands of suture so that one of the cannulated spheres is fixed whereas the other cannulated sphere is moveable relative to one of the flexible strands;
   accessing the first socket from an articular surface of the first bone to insert one cannulated sphere through an opening proximal to the articular surface of the first bone;
   accessing the second socket from an articular surface of the second bone to insert the other cannulated sphere through an opening proximal to the articular surface of the second bone; and
   pulling one of the flexible strands so that a length of the flexible strand extending between the two cannulated spheres is about equal to a length of a tissue to be positioned within the first and second sockets.

10. The method of claim 9, wherein the first bone is a femur and the second bone is a tibia.

* * * * *